| United States Patent [19] | [11] Patent Number: 5,518,884 |
|---|---|
| Spears et al. | [45] Date of Patent: May 21, 1996 |

[54] NUCLEIC ACID SEQUENCES SPECIFIC FOR MYCIBACTERIUM KANSASII

[75] Inventors: Patricia A. Spears, Raleigh, N.C.; Daryl D. Shank, Bel Air, Md.

[73] Assignee: Becton, Dickinson and Company, Franklin Lakes, N.J.

[21] Appl. No.: 203,534

[22] Filed: Feb. 28, 1994

[51] Int. Cl.$^6$ .............................. C12Q 1/68; C12P 19/34; C07H 21/00
[52] U.S. Cl. .......................... 435/6; 435/91.2; 536/24.32
[58] Field of Search ................... 435/6, 91.2; 536/24.32

[56] References Cited

PUBLICATIONS

Huang, et al 1991, J. Clin. Microbiol., 29, 2125–2129.
Ross, et al 1992, J.Clin. Microbiol., 30, 2930–2933.
Rogall et al. 1990, J. Gen. Microbiol., 136, 1915–1920.
Boddinghaus et al 1990, J. Clin. Microbiol., 28, 1751–1759.
Yang et al. 1993, J. Clin. Microbiol., 31, 2769–2772.
Gen Bank Loc; ORZCAMA, BMACTAZ, XLACASR, HUMNB1, SLMACT 35.

*Primary Examiner*—W. Gary Jones
*Assistant Examiner*—David Schreiber
*Attorney, Agent, or Firm*—Donna R. Fugit

[57] ABSTRACT

Oligonucleotide probes and primers which exhibit *M. kansasii*-specificity in nucleic acid hybridization assays and in nucleic acid amplification reactions are provided. The full-length *M. kansasii*-specific sequence, identified herein as clone MK7, is 493 base pairs in length and has a GC content of 63%. Several *M. kansasii*-specific subsequences of MK7 are also provided. The probes and primers are useful in assays for species-specific detection and identification of *M. kansasii*.

18 Claims, 1 Drawing Sheet

281 BASE PAIR REGION OF pMK7

```
                                                         HINC II
                                              HINC II       \
                                                  \          S1.2 (#7)
                                         HINC II        S1.1 (#6)
213        B1 (#4)                          \           S1 (#2)
GATCCGCCGC CGCACAACTG CTGGCCGGGC ATGACACCGA CCCATCAGTC AGCGAATCCT CCGCTGCATC AAATG

AATCCACAGT CATCGACCTG TCCGTCTATA GCGGGCAGCC CAGAAAAGGA CCTTAAATGA CCGCTACCCA CGCAC
         S2 (#3)                                                       B2.1 (#8)
                      HINC II

GCCGAAGACC AGCCGGGCCG CGAGTACCGA GTCGCCGGCT CAGTCGGCCA GTCGCTATCA GCACGTGCGC TCGCA
                                                          B2 (#5)

493
TCTGGCCGAA CTCAAACTGC ACGCCGCCGC TGAAGCCCTG CCCGCCGTCC TGGATC
```

NUCLEIC ACID SEQUENCES SPECIFIC FOR MYCIBACTERIUM KANSASII

FIELD OF THE INVENTION

The present invention relates to oligonucleotide probes and amplification primers, and particularly relates to oligonucleotide probes and primers which hybridize in a species-specific manner to *Mycobacterium kansasii* nucleic acids.

BACKGROUND OF THE INVENTION

The Mycobacteria are a genus of bacteria which are acid-fast, non-motile, gram-positive rods. The genus comprises several species which include, but are not limited to, *Mycobacterium africanum, M. avium, M. bovis, M. bovis-BCG, M. chelonae, M. fortuitum, M. gordonae, M. intracellulare, M. kansasii, M. microti, M. scrofulaceum, M. paratuberculosis* and *M. tuberculosis.* Certain of these organisms are the causative agents of disease. For the first time since 1953, cases of mycobacterial infections are increasing in the United States. Of particular concern is tuberculosis, the etiological agent of which is *M. tuberculosis.* However, infections caused by Mycobacteria other than tuberculosis (MOTT) have also been increasing. Many of these new cases are related to the AIDS epidemic, which provides an immune compromised population which is particularly susceptible to infection by Mycobacteria. *Mycobacterium avium, Mycobacterium kansasii* and other non-tuberculosis mycobacteria have been found as opportunistic pathogens in HIV-infected and other immune compromised patients. There is an increasing need for rapid diagnosis of these infections, as they can disseminate rapidly and may be fatal within a short period of time.

At the present time the diagnosis of mycobacterial infections is dependent on acid-fast staining and cultivation of the organism, followed by biochemical assays. These procedures are time-consuming, and a typical diagnosis using conventional culture methods can take as long as six weeks. Automated culturing systems such as the BACTEC system (Becton Dickinson Microbiology Systems, Sparks, Md.) can decrease the time for diagnosis to one to two weeks. However, there is still a need to reduce the time required for diagnosing mycobacterial infections to less than a week, preferably to about one day. Oligonucleotide probe based assays such as Southern hybridizations or dot blots are capable of returning a rapid result (i.e., in one day or less). Genus- and species-specific oligonucleotide probes can also be used in direct assays of clinical samples by nucleic acid amplification. However, both of these rapid detection and identification methods require oligonucleotide probes which are specific for the genus Mycobacteria (tuberculosis and non-tuberculosis) or specific for a particular mycobacterial species if specific identification of the organism is desired.

Conventional laboratory identification of *Mycobacterium kansasii* relies upon biochemical testing and determination of growth characteristics. These include catalase production, urease activity, TWEEN hydrolysis, nitrate reduction and the ability of the bacterium to produce pigment when exposed to light (photochromogenicity). Because several other mycobacterial species exhibit a similar biochemical profile, photochromogenicity is customarily relied upon as the conclusive characteristic for identification of *Mycobacterium kansasii.* However, determination of photochromogenicity requires a pure culture of the organism and this phenotype can be variable, subjective and difficult to determine reliably. For these reasons, there have been attempts to identify *Mycobacterium kansasii* by species-specific hybridization or nucleic acid amplification using oligonucleotide probes. Z. H. Huang, et al. (1991. *J. Clin. Microbiol.* 29, 2125–2129) have reported a DNA probe obtained from a genomic library with a degree of species-specificity for *Mycobacterium kansasii.* This clone (pMK1-9) showed some cross-hybridization with other species, including *M. gastri,* and did not detect a genetically distinct subgroup of *M. kansasii.* The nucleotide sequence of pMK1-9 was not reported, nor was the gene from which it may have been derived identified. B. C. Ross, et al. (1992. *J. Clin. Microbiol.* 30, 2930–2933) also reported identification of genetically distinct subspecies of *M. kansasii* using the pMK1-9 probe, a 65kDa antigen gene probe and a commercial DNA probe test employing probes which specifically hybridize to rRNA (ACCU-PROBE, Gen-Probe, San Diego, Calif.). Amplification primers which hybridize to the 16S rRNA gene were used to sequence and compare the 16S rRNA gene sequences of the *M. kansasii* variants studied. M. Yang, et al. (1993. *J. Clin. Microbiol.* 31, 2769–2772) have reported isolation of an *M. kansasii*-specific probe from a clinical isolate. This probe (p6123) hybridized to all *M. kansasii* strains tested, including the subgroup which is pMK1-9 negative.

T. Rogall, et al. (1990. *J. Gen. Microbiol.* 136, 1915–1920) used the 16S rRNA sequence in a polymerase chain reaction (PCR) based sequencing strategy for identification of mycobacterial species. However, these primers could not be used to differentiate *M. gastri* from *M. kansasii* because the 16S rRNA sequence from these two species is identical in spite of their differing phenotypic characteristics. Similar studies have been published by B. B öddinghaus, et al. ( 1990. *J. Clin. Microbiol.* 28, 1751–1759), who reported oligonudeotides derived from 16S rRNA sequences which are specific for the *M. tuberculosis* group, *M. avium-M. paratuberculosis,* and *M. intracellulare.* Unique sequence stretches within 16S rRNA sequences were identified by sequence comparisons for *M. kansasii,* including *M. gastri, M. simiae,* and *M. scrofulaceum.*

The present invention provides nucleic acid sequences useful as oligonucleotide probes and amplification primers for species-specific detection and identification of *Mycobacterium kansasii.* Species-specificity means that the inventive probes and primers hybridize to *M. kansasii* nucleic acids with little or no cross-hybridization to the nucleic acids of other species of mycobacteria or to the nucleic acids of closely related microorganisms such as *Rhodococcus rhodochrous* and *Nocardia asteroides.* The sequences of these probes and primers and the fragment of *M. kansasii* genomic DNA from which they are derived are distinct from the *M. kansasii*-specific nucleic acid sequences previously reported. The probes and primers may be used after culturing a sample as a means for confirming identity of the culture. Alternatively, the probes and primers may be used prior to culturing in detection and identification methods for bacterial DNA based on nucleic acid hybridization or nucleic acid amplification. In either case, the inventive probes, primers and diagnostic methods provide a means for rapidly discriminating between *M. kansasii* and other species of mycobacteria, allowing the practitioner to rapidly identify this microorganism without resorting to the time-consuming phenotypic and biochemical procedures customarily relied upon. Such rapid identification of the specific etiological agent involved in a mycobacterial infection provides information which can be used to determine appropriate therapy within a short period of time. Ninety-four percent of the clinical and environmental *M. kanasii* isolates tested were positive in amplification assays using the inventive amplification primers. The *M. kansasii*-specific sequences of the invention are distinct from p6123 and pMK1-9 and are derived from a gene or a portion of the *M. kansasii* genome which was previously unknown.

SUMMARY OF THE INVENTION

The present invention provides oligonucleotide probes and primers which exhibit *M. kansasii*-specificity in nucleic acid hybridization assays and in nucleic acid amplification reactions. The full-length *M. kansasii*-specific sequence, identified herein as clone MK7, is 493 base pairs in length and has a GC content of 63%. Several *M. kansasii*-specific subsequences of MK7 were also identified and used to design hybridization probes and amplification primers for use in assays for species-specific detection and identification of *M. kansasii*.

DETAILED DESCRIPTION OF THE INVENTION

The *M. kansasii*-specific nucleotide sequence of the present invention was derived from an *M. kansasii* genomic library and is 493 base pairs in length with a GC content of 63% (SEQ. ID NO:1). *M. kansasii*-specific subsequences of SEQ ID NO:1 useful as hybridization probes and amplification primers were also identified. These probes and primers may either be hybridized directly to mycobacterial DNA and detected, or they may be used as primers in nucleic acid amplification reactions to produce *M. kansasii*-specific amplification products which may then be detected. That is, it should be understood that the *M. kansasii*-specific oligonucleotides used as hybridization probes by way of example may also be used as *M. kansasii*-specific amplification primers in nucleic acid amplification protocols, and vice versa. The terms "probe" and "primer" are therefore used herein as an indication of the function of the oligonucleotide in the reaction being described. Any given *M. kansasii*-specific nucleotide sequence encompassed by the invention may be used as either a probe or a primer as appropriate for the detection method.

*M. kansasii*-specific probes and primers in addition to those specifically disclosed herein may also be derived from the MK7 sequence using routine methods and criteria appropriate for any particular assay format employed. In general, these probes and primers will be at least about 10–15 nucleotides in length, preferably about 15–20 nucleotides in length. Probes and primers may be either deoxyribonucleic acid (DNA) or ribonucleic acid (RNA) and may have either a naturally-occurring sugar-phosphate backbone or a backbone modified to include phosphorothioates, dithionates, alkyl phosphonates or α-nucleotides as is known in the art. The probes and primers may be produced by chemical synthesis of the oligonucleotides, by cloning and amplification in a transformed host cell, or by other means known in the art.

Probes and primers according to the invention are hybridized to nucleic acids in samples suspected of containing mycobacteria. The samples may comprise isolated nucleic acids, isolated microorganisms, or they may be clinical samples. Typically, clinical samples are in the form of a biological fluid or tissue, e.g., sputum, bronchial washings, gastric washings, blood, milk, lymph, skin and soft tissues. Prior to hybridization with the probes and primers of the invention, samples suspected of containing intact microorganisms rather than free nucleic acids are generally treated using methods known in the art to release nucleic acids from any microorganisms present. In addition, sputum samples are typically liquified prior to releasing nucleic acids for analysis. As mycobacteria infect both human and non-human animal species, the present invention is applicable to both human and veterinary diagnostic procedures and the sample may be obtained from either source. As humans are susceptible to infection from a variety of Mycobacteria, including *M. tuberculosis, M. kansasii, M. avium, M. intracellulare, M. scrofulaceum* and *M. fortuitum,* the instant probes, primers and methods may be used to rapidly identify cases in which *M. kansasii* is the etiologic agent, thereby aiding in selection of an appropriate therapy.

The oligonucleotide probes and primers are used to detect and/or identify *Mycobacterium kansasii* by hybridization to mycobacterial nucleic acid or by amplification of mycobacterial nucleic acid target sequences. In one embodiment, the probes are used in hybridization methods for direct detection of target *M. kansasii* nucleic acid. These methods include Southern blots for detection of DNA, Northern blots for detection of RNA and dot blots for detection of either DNA or RNA. These methods are generally well-known in the art and are described in *Molecular Cloning: A Laboratory Manual,* 2nd ed., J. Sambrook, E. F. Fritsch and T. Maniatis, Cold Spring Harbor Laboratory Press, 1989. In a second embodiment, the presence of *M. kansasii* in a sample is detected and/or identified by species-specific amplification of target nucleic acid sequences. In this embodiment, the probes or primers of the invention are used in conventional nucleic acid amplification protocols. Any amplification protocol which relies on cyclic hybridization of primers to the target nucleic acid may be used, e.g., PCR (U.S. Pat. Nos. 4,683,195; 4,683,202; 4,800,159; 4,965,188), ligase chain reaction (LCR) (R. Weiss (1991) Science 254:1292), strand displacement amplification (SDA) (G. Walker, et al. (1992) PNAS 89:392–396; G. Walker, et al. (1992) Nucleic Acids Res. 20:1691–1696), nucleic acid based sequence amplification (NASBA) (U.S. Pat. No. 5,130,238 to Cangene), transcription based amplification (D. Kwoh, et al. (1989) PNAS 86:1173–1177), self-sustained sequence replication (J. Guatelli, et al. (1990) PNAS 87:1874–1878) or the Qβ replicase system (P. Lizardi, et al. (1988) BioTechnology 6:1197–1202). Adjacent primers suitable for use in LCR can be easily selected from SEQ ID NO:1. However, preferred amplification methods for use with the primers of the invention are methods which utilize cyclic hybridization of primers to the target sequence, extension of the primers using the target sequence as a template and displacement of the extended primers from the target sequence, e.g., PCR and SDA.

An amplification primer is a primer for amplification of a target sequence by primer extension or ligation of adjacent primers hybridized to the target sequence. For amplification by SDA, the oligonucleotide primers are preferably selected such that the GC content is low, preferably less than 70% of the total nucleotide composition of the probe. Similarly, for SDA the target sequence preferably has a low GC content to minimize secondary structure. The 3' end of an SDA amplification primer (the target binding sequence) hybridizes at the 3' end of the target sequence. The target binding sequence confers target specificity on the amplification primer, and the *M. kansasii*-specific sequences of the invention may therefore be used as target binding sequences in SDA amplification primers. The SDA amplification primer further comprises a recognition site for a restriction endonuclease near its 5' end. The recognition site is for a restriction endonuclease which will nick one strand of a DNA duplex when the recognition site is hemimodified, as described by Walker, et al. (1992. PNAS 89, 392–396). The SDA amplification primer may also comprise additional sequences 5' to the restriction endonuclease recognition site to allow the appropriate restriction endonuclease to bind to its recognition site. For the majority of the SDA reaction, the amplification primer is responsible for exponential amplification of the target sequence. For other amplification methods which do not require attachment of specialized sequences to the ends of the target, the amplification primer generally consists of only the target binding sequence.

A bumper primer is a primer used in SDA which anneals to a target sequence upstream of the amplification primer such that extension of the bumper primer displaces the downstream primer and its extension product. Extension of bumper primers is one method for displacing the extension products of amplification primers, but heating is also suitable.

The terms target or target sequence refer to nucleic acid sequences amplifiable by amplification primers. These include the original nucleic acid sequence to be amplified, the complementary second strand of the original nucleic acid sequence to be amplified, and either strand of a copy of the original sequence which is produced by the amplification reaction. These copies also serve as amplifiable target sequences by virtue of the fact that they also contain copies of the original target sequences to which the amplification primers hybridize.

As nucleic acids do not require complete complementarity in order to hybridize, it is to be understood that the probe and primer sequences herein disclosed may be modified to some extent without loss of utility as *M. kansasii*-specific probes and primers. As is known in the art, hybridization of complementary and partially complementary nucleic acid sequences can be obtained by adjustment of the hybridization conditions to increase or decrease stringency (i.e., adjustment of hybridization temperature or salt content of the buffer). Such minor modifications of the disclosed sequences and any necessary adjustments of hybridization conditions to maintain *M. kansasii*-specificity require only routine experimentation and are well within the ordinary skill in the art.

The nucleic acid products of amplification using the inventive primers (i.e., the amplification products or extension products) may be detected by a characteristic size, for example on polyacrylamide or agarose gels stained with ethidium bromide. Alternatively, *M. kansasii* nucleic acid in a sample or specifically amplified *M. kansasii* target sequences may be detected by hybridization to the inventive probes and primers. For detection by hybridization the oligonucleotide probes are typically tagged with a detectable label. The detectable label is a moiety which can be detected either directly or indirectly as an indication of hybridization of the probe to the target nucleic acid. For direct detection of the label, probes may be tagged with a radioisotope and detected by autoradiography or tagged with a fluorescent moiety and detected by fluorescence as is known in the art. Alternatively, the probes may be indirectly detected by tagging with a label which requires additional reagents to render it detectable. Indirectly detectable labels include, for example, chemiluminescent agents, enzymes which produce visible reaction products and ligands (e.g., haptens, antibodies or antigens) which may be detected by binding to labeled specific binding partners (e.g., antibodies or antigens/haptens). Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to, or including such labels in, oligonucleotides are well known in the art and any of these methods are suitable for use in the present invention.

For detection of amplified target sequences, the primers used in the amplification reaction may be tagged and used as detector probes because the primers are incorporated into the amplification product. Alternatively, at least one tagged probe different from the amplification primers may be used as a probe for detection of amplified target sequences by hybridization. This probe should be selected to hybridize to a sequence in the target which is between the amplification primers, i.e., an internal probe. Alternatively, either the primer or the internal probe may be tagged and extended for detection of amplification products as described by Walker, et al., supra.

For convenience, probes for species-specific detection and identification of *M. kansasii* may be packaged in the form of a kit which may further include other components and reagents for performing the detection methods. By way of example, such a kit contains at least one probe or at least one pair of amplification primers according to the present invention. For detection by hybridization, a hybridization solution such as 6X SSC (0.9M sodium chloride, 0.09M sodium citrate, pH 7.0), 0.1M EDTA pH 8.0, 5X Denhardt's solution (0.1% w/v FICOLL TYPE 400, 0.1% w/v polyvinylpyrrolidone, 0.1% w/v bovine serum albumin) and 100 µg/ml sheared denatured salmon sperm DNA, or other reagents known to be useful for probe hybridization may also be included. See *Molecular Cloning: A Laboratory Manual*, supra. Alternatively, reagents appropriate for use with one of the known nucleic acid amplification methods may be included with *M. kansasii*-specific amplification primers. The components of the kit are packaged together in a common container, typically including instructions for performing a specific embodiment of the inventive methods. Additional, optional components may also be included in the kit, e.g., a second probe tagged with a label suitable for use as a detection probe, and reagents or means for performing detection of the label.

The following experimental examples are given as illustrations of certain embodiments of the invention. They are not to be construed in any way as limiting the invention as defined by the appended claims.

The mycobacteria used in the following examples were *M. avium* ATCC25291, *M. bovis* CDC4, *M. chelonae* TMC1543, *M. flavescens* LCDC2601, *M. fortuitum* TMC1529, *M. gastri* LCDC1301, *M. gordonae* TMC1318, *M. intracellulare* ATCC13950, *M. kansasii* TMC1201, *M. kansasii* LCDC711, *M. kansasii* LCDC714, *M. kansasii* LCDC715, *M. kansasii* LCDC724, *M. kansasii* LCDC725, *M. malomense* CDC93, *M. marinum* LCDC801, *M. microti* LCDC203, *M. nonchromogenicus* LCDC1401, *M. scrofulaceum* TMC1302, *M. szulgai* TMC1328, *M. terrae* TMC1450, *M. tuberculosis* ATCC27294 and *M. xenopi* LCDC 1901. Non-mycobacteria used were *Bordetella pertussis* ATCC8467, *Corynebacterium diphtheriae* ATCC11913, *Escherichia coli* ATCC11775, *Nocardia asteroides* ATCC3308, *Rhodococcus rhodochrous* ATCC13808. Mycobacteria strains were cultured in BACTEC vials in Middlebrook 7H9 media, then heat killed at 70° C. for 4 hours. Genomic DNA was isolated as previously described (S. Visuvanathan, et al. 1989. *J. Microbiol. Mtds.* 10,59–64). Non-mycobacteria strains were cultured in Luria broth or other suitable media. Genomic DNA was isolated by the CTAB mini-prep method (F. M. Ausubel, et al. 1987. *Current Protocols in Molecular Biology*, Greene Publishing Associates and Wiley-Interscience, NY).

EXAMPLE 1

CLONING OF MK7

A plasmid library of *M. kansasii* DNA was constructed and screened for genus- and species-specific clones. To construct the library, *M. kansasii* genomic DNA (strain TMC 1201) was restricted with Sau3AI (Gibco BRL). The fragment sizes generated ranged from about 1.4 kb to less than 200 base pairs. The cloning vector, BLUESCRIPT SK+ (Stratagene), was digested with BamHI (Gibco BRL) and phosphatased using alkaline phosphatase from calf intestine (CIAP-Boehringer Mannheim Biochemicals). The genomic fragments (750 ng) were ligated to 20 ng of the prepared vector in 50 mM Tris-HCl pH 7.5, 7 mM $MgCl_2$, 1 mM DTT, 1 mM ATP and 1 Unit/10 µl T4 DNA ligase (Gibco BRL). The ligation was allowed to proceed overnight at 15° C. and was then used to transform JM109 competent cells (Stratagene). One thousand independent transformants were isolated. Of these 1000 clones, 15 were selected for screening genomic blots consisting of various mycobacterial and non-mycobacterial DNA's.

Southern blots were performed as follows. Genomic DNA from each mycobacterial and non-mycobacterial species was digested with PstI (Gibco BRL), separated on a 0.8% agarose gel and transferred to a nylon membrane (Gibco BRL nylon-1) (Maniatis, et al., supra). The membranes were UV-crosslinked (Stratalinker) and hybridized with $^{32}P$-labeled probes (i.e., the inserts isolated from the 15 selected clones) as described by Maniatis, et al., supra. The probes were labeled by random primers (Boehringer Mannheim Biochemicals) using $[\alpha-^{32}P]$-deoxyadenosine triphosphate and $[\alpha-^{32}P]$-deoxycytidine triphosphate (NEN-DuPont). The hybridized membranes were washed at high stringency, followed by exposure to XAR-5 film for 1–7 days (Maniatis, et al., supra). Of the 15 clones, MK7 was found to hybridize specifically to *M. kansasii* DNA. This clone was sequenced on an Applied Biosystems 373A DNA Sequencer using the TAQ DYE PRIMER or TAQ DYE TERMINATOR CYCLE SEQUENCING KIT (ABI) and SEQUENASE (United States Biochemical) as recommended by the manufacturers. The nucleotide sequence of MK7 is 493 base pairs in length and has a GC content of 63%. This sequence is given herein as SEQ ID NO:1.

MK7 contains three internal Sau3AI sites (GATC). These may have resulted from a partial digestion with Sau3AI or may be the result of ligation of multiple Sau3AI fragments which are not continuous in the genome. While the possibility that MK7 comprises discontinuous segments of the *M. kansasii* genome is not a concern when using this clone as a hybridization probe, for nucleic acid amplification the target sequences must be continuous. A 281 base pair segment of MK7 between two of the Sau3AI sites was therefore selected for further analysis and design of *M. kansasii*-specific amplification primers. This entire 281 bp fragment (nucleotides 213–493 of MK7) exhibited species specificity by hybridization analysis on Southern blots. That is, it hybridized to *M. kansasii* nucleic acids but did not hybridize to the nucleic acids of other mycobacterial and non-mycobacterial organisms tested. These included *M. avium, M. boris, M. fortuitum, M. gastri, M. gordonae, M. intracellulare, M. tuberculosis, Bordetella pertussis, Corynebacterium diphtheriae, Escherichia coli, Nocardia asteroides* and *Rhodococcus rhodochrous*. The 281 bp fragment was then divided into two smaller subfragments designated A and B. Fragment A comprises nucleotides 221–370 of MK7 and fragment B comprises nucleotides 351–490. Both fragments A and B maintain species-specificity by hybridization analysis on Southern blots and hybridize to a 2.75 kb PstI fragment of *M. kansasii* genomic DNA.

The sequence of the 281 bp fragment was compared to known nucleotide sequences by searching GENBANK 75, UEMBL 33-75 and N-GENESEQ 9 and no similar sequences were found.

EXAMPLE 2

STRAND DISPLACEMENT AMPLIFICATION

Oligonucleotides for use as amplification primers were synthesized on an Applied Biosystems 380B Synthesizer as recommended by the manufacturer. The oligonucleotides were deprotected at 50° C. and gel purified as previously described (Ausubel, et al.). Strand Displacement Amplification (SDA) reactions were performed as previously described by Walker, et al., supra, in a 50 µl volume consisting of 6–8 mM $MgCl_2$, 0.2 mM each dGTP, dCTP and α-thio dATP, 0.5 mM dUTP, 100 µg/ml acetylated bovine serum albumin, 1 ng/µl human placental DNA, 50 mM potassium phosphate pH 7.6, 0.5 µM $S_1$ and $S_2$ primers, 0.05 µM $B_1$ and $B_2$ primers, 3 units/µl HincII, 0.1 unit/µl exo⁻ Klenow DNA polymerase (United States Biochemical) and varying amounts of target DNA. The reactions also contained either 15% (v/v) dimethylsulfoxide (DMSO) or 20–25% (v/v) glycerol. Prior to the addition of HincII, exo⁻ Klenow and $MgCl_2$, the reactions were heated at 95° C. for 2 minutes to denature the target DNA, followed by 2 minutes at 37°–40° C. to anneal the primers. Following the addition of the enzymes and $MgCl_2$ the reactions were incubated at 37°–40° C. for 2 hours for amplification. Amplification was terminated by heating for 2 minutes at 95° C. Amplification products were detected by primer extension of a $^{32}P$-labeled probe and analyzed by denaturing polyacrylamide gel electrophoresis as described by Walker, et al., supra.

Figure 1:
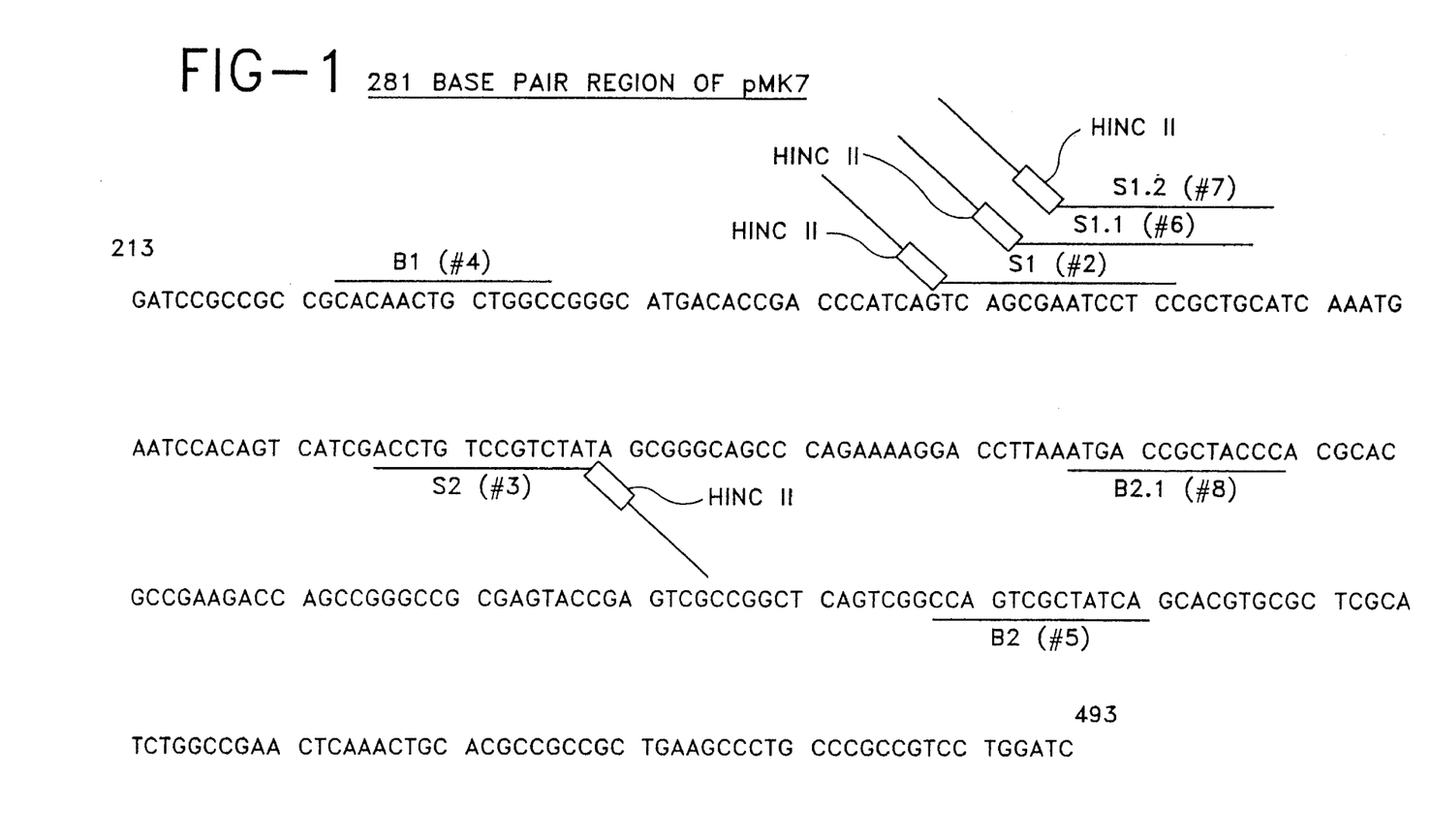
FIG. 1 depicts the 281 bp fragment of MK7 and illustrates hybridization of representative primers to this fragment.

The amplification primers were selected from within the sequence of the 281 bp fragment described above. In one SDA reaction, SEQ ID NO:2 and SEQ ID NO:3 were used as amplification primers (i.e., $S_1$ and $S_2$) and SEQ ID NO:4 and SEQ ID NO:5 were used as bumper primers (i.e., $B_1$ and $B_2$). This set of primers was designated Primer Set #1 and the locations of hybridization within the 281 bp fragment are shown in FIG. 1. Amplification using this primer set was *M. kansasii* specific and an amplification product was detected only when *M. kansasii* nucleic acids were used as the target. No amplification product was detected when *M. avium, M. bovis, M. chelonae, M. fortuitum, M. gastri, M. gordonae, M. intracellulare, M. malomense, M. marinum, M. microti, M. nonchromogenicum, M. tuberculosis* or *M. xenopi* nucleic acids were used as targets for amplification. The sensitivity was 20 genome molecules of *M. kansasii* DNA.

This same primer set was used to test specificity of amplification using other strains of *M. kansasii* as targets. Amplification products were detected from *M. kansasii* TMC1201, LCDC711, LCDC714, LCDC715 and LCDC725. However, *M. kansasii* LCDC724 did not amplify with this primer set. The 5' end of the rDNA gene from LCDC724 was therefore amplified by PCR and sequenced (Boddinghaus, et al.; Meier, et al.; Rogall, et al.). The sequence obtained was compared to the *M. kansasii* DSM 43224 rDNA gene sequence as reported by GENBANK and found to be different. There were two deletions and three mismatches within 13 base pairs corresponding to nucleotides 75–87 of the corresponding *E. coli* gene. Biochemical tests of the LCDC724 strain are identical to typical *M. kansasii*, however, Ross, et al. have suggested that LCDC724 represents a distinct subspecies. The 5 bp difference in the rDNA sequence could indicate either that LCDC724 is a distinct subspecies of *M. kansasii* or that it is a different species of mycobacteria. Primer Set #1 therefore amplifies all typical *M. kansasii* strains tested, but does not amplify an atypical genetically distinct subspecies of *M. kansasii* identified as LCDC724.

Additional primer sets were designed in an attempt to increase the sensitivity of the amplification assay. First, two additional $S_1$ primers based on MK7 were designed. SEQ ID NO:6 is shifted four nucleotides downstream (i.e., 3') of SEQ ID NO:2, as shown in FIG. 1. SEQ ID NO:7 is shifted six nucleotides downstream of SEQ ID NO:2, also as shown in FIG. 1. A new $B_2$ primer (SEQ ID NO:8) was also designed to hybridize closer to the amplified region. Primer Set #2 consisted of SEQ ID NO:6, SEQ ID NO:3, SEQ ID NO:4 and SEQ ID NO:8. This primer set showed the same sensitivity (20 genome molecules of *M. kansasii* DNA) and specificity as Primer Set #1.

Primer Set #3 consisted of SEQ ID NO:7, SEQ ID NO:3, SEQ ID NO:4 and SEQ ID NO:8. In SDA reactions this primer set showed a 10 fold increase in sensitivity (2 genome molecules of *M. kansasii* DNA) while retaining *M. kansasii* species specificity. No cross-reactivity with *M. tuberculosis*, *M. bovis*, *M. avium*, *M. intracellulare*, *M. gastri*, *M. fortuitum*, *M. chelonae*, *M. szuglia*, *M. malomense*, *M. scrofulaceum*, *M. flavence*, *M. xenopi*, *M. terrae*, *M. marinum* or *M. gordonae* was detected. Primer Set #3 amplifies a target sequence in typical *M. kansasii* DNA, e.g., strains TMC1201, LCDC711, LCDC714, LCDC715 and LCDC725. However, it does not amplify *M. kansasii* LCDC724, the proposed genetically distinct subspecies of *M. kansasii*.

SDA was used as the amplification method in this example, however, the target binding sequences of the amplification primers of the example may be used alone as amplification primers in other methods of amplification which do not require attachment of specialized sequences to the target sequence (e.g., PCR). That is, for use in amplification methods such as PCR, SEQ ID NO:9 may be substituted for SEQ ID NO:2, SEQ ID NO:10 may be substituted for SEQ ID NO:3, SEQ ID NO:11 may be substituted for SEQ ID NO:6 and SEQ ID NO:12 may be substituted for SEQ ID NO:7 as amplification primers in the appropriate amplification reaction. Similarly, any other desired sequence may be added to the target binding sequence of the amplification primers to provide a desired function, e.g., a restriction endonuclease recognition site or homopolymer tails (to facilitate cloning), a protein binding site, etc.

As shown in FIG. 1, there is a potential open reading frame (ORF) which begins at nucleotide 344 and continues to the end of the clone at nucleotide 493. The initiation codon, ATG, is followed by an A which could serve as a stop codon (TGA) for another ORF which begins upstream of the 281 bp fragment. Upstream of the ATG, at –7, is a potential ribosomal binding site AGAAAAGGA (Shine-Delgarno sequence). There are also putative promoters at –26 (TATA), –38 (TCGACC) and –48 (TCCACA). These potential promoter sequences are not ideal by *E. coli* standards, however, they compare well with other mycobacterial promoters (McFadden). Also, with a potential overlap from an alternate reading frame, there may not be a need for a promoter sequence in this case. The hypothetical protein sequence encoded by the ORF from nucleotides 344–493 is 50 amino acids in length. No similar protein sequence was found when this hypothetical sequence was searched in the SWISSPROT 24 database.

To confirm that the probes and primers of the invention were useful for detection of a wide variety of *M. kansasii* strains, Strand Displacement Amplification was performed as described above on 66 clinical and environmental isolates of *M. kansasii* originating from eight different countries. The samples represented a selection of those described by M. Yang, et al. (1993, supra). Primer Set #3 (SEQ ID NO:7, SEQ ID NO:3, SEQ ID NO:4, SEQ ID NO:8) was used for the amplification and the results are shown in the following table.

TABLE

| LAB NO. | COUNTRY OF ORIGIN | SAMPLE ORIGIN | AMPLIFICATION |
|---|---|---|---|
| 41708(A) | Australia | Clinical | Pos. |
| 57 | Australia | Clinical | Pos. |
| 139856 | Solomon Islands | Clinical | Pos. |
| 41708(B) | Australia | Clinical | Pos. |
| 135328 | Australia | Clinical | Pos. |
| 4792 | Australia | Clinical | Pos. |
| 139855 | Solomon Islands | Clinical | Pos. |
| 126273 | Australia | Clinical | Pos. |
| 7193 | Australia | Clinical | Pos. |
| p21-19 | Japan | Clinical | Pos. |
| p21-20 | Japan | Clinical | Pos. |
| p21-16 | Japan | Clinical | Pos. |
| p21-17 | Japan | Clinical | Pos. |
| lab#27 | Japan | Clinical | Pos. |
| p21-23 | Japan | Clinical | Pos. |
| lab#17 | Japan | Clinical | Pos. |
| p21-22 | Japan | Clinical | Pos. |
| p21-28 | Japan | Clinical | Pos. |
| p21-18 | Japan | Clinical | Pos. |
| lab#14 | Japan | Clinical | Pos. |
| 176726 | England | Respiratory | Pos. |
| 176715 | England | Respiratory | Pos. |
| 176723 | England | Respiratory | Pos. |
| 176729 | England | Respiratory | Pos. |
| 176733 | England | Clinical | Pos. |
| 182542 | USA | Clinical | Pos. |
| 182554 | USA | Clinical | Pos. |
| 182545 | USA | Clinical | Pos. |
| 182537 | USA | Clinical | Pos. |
| 182548 | USA | Clinical | Pos. |
| 182535 | USA | Clinical | Neg. |
| 182544 | USA | Clinical | Pos. |
| 182540 | USA | Clinical | Pos. |
| 182542 | USA | Clinical | Pos. |
| 182539 | USA | Clinical | Pos. |
| 182549 | USA | Clinical | Pos. |
| 177 | South Africa | Clinical | Pos. |
| 3910 | South Africa | Clinical | Pos. |
| 4142 | South Africa | Clinical | Pos. |
| 580 | South Africa | Clinical | Pos. |
| 148829 | Australia | Environmental | Pos. |
| 148832 | Australia | Environmental | Pos. |
| 169192 | Australia | Environmental | Pos. |
| 90-1732 | Switzerland | Urine | Pos. |
| 6235 | Belgium | Clinical | Pos. |
| 89-4247 | Switzerland | Urine | Weak Pos. |
| 90-2882 | Switzerland | Urine | Neg. |
| 89-4235 | Switzerland | Urine | Neg. |
| 6235(A) | Belgium | Clinical | Pos. |
| 90-3191 | Switzerland | Urine | Pos. |

TABLE-continued

| LAB NO. | COUNTRY OF ORIGIN | SAMPLE ORIGIN | AMPLIFI-CATION |
|---|---|---|---|
| 89-2169 | Switzerland | Urine | Pos. |
| 88-6646 | Switzerland | Urine | Pos. |
| 88-2771 | Switzerland | Urine | Pos. |
| 90-0752 | Switzerland | Urine | Pos. |
| 2966 | Switzerland | Clinical | Neg. |
| 6231 | Belgium | Urine | Pos. |
| 6232 | Belgium | Clinical | Pos. |
| 89-1652 | Switzerland | Urine | Pos. |
| 89-2621 | Switzerland | Sputum | Weak Pos. |
| 90/224 | Australia | Clinical | Pos. |
| 15589 | Australia | Clinical | Pos. |
| 27607 | Australia | Clinical | Pos. |
| 134067 | Australia | Clinical | Pos. |
| 2752 | Australia | Clinical | Pos. |
| 135328 | Australia | Clinical | Pos. |
| 6738 | Australia | Clinical | Pos. |

M. Yang, et al., supra, reported that 88% of their strains were positive using the commercial ACCU-PROBE test for *M. kansasii* and that 100% were positive by hybridization to the p6123 probe. The inventive probes and primers detect about 94% of the M. Yang, et al. *M. kansasii* strains. Applicants' SEQ ID NO:1 and the probes and primers derived from this sequence are distinct from p6123 and the ACCU-PROBE probes and have a unique nucleotide sequence not previously reported. SEQ ID NO:1 also has the advantage of being more highly conserved among *M. kansasii* strains than p6123 and therefore assay results provide a clearer distinction between positive and negative samples. That is, assays using the primers and probes derived from SEQ ID NO:1 are either very clearly positive or very clearly negative, making interpretation of the assay results easier. In contrast, although 100% of *M. kansasii* strains test positive using p6123, the greater variability of this sequence results in a broad range of degrees of positivity which complicates interpretation and may obscure the distinction between positive and negative.

What is claimed is:

1. An oligonucleotide consisting of SEQ ID NO:1 or its complement.

2. An oligonucleotide consisting of nucleotides 213–493 of SEQ ID NO:1 or the complement of nucleotides 213–493 of SEQ ID NO:1.

3. An oligonucleotide consisting of nucleotides 221–370 of SEQ ID NO:1 or the complement of nucleotides 221–370 of SEQ ID NO:1.

4. An oligonucleotide consisting of nucleotides 351–490 of SEQ ID NO:1 or the complement of nucleotides 351–490 of SEQ D NO:1.

5. An oligonucleotide consisting of SEQ ID NO:2, SEQ ID NO:3, SEQ ID NO:4, SEQ ID NO:5, SEQ ID NO:6, SEQ ID NO:7 or SEQ ID NO:8.

6. An oligonucleotide consisting of SEQ ID NO:9, SEQ ID NO:10, SEQ ID NO:11 or SEQ ID NO:12.

7. A method for detecting *M. kansasii* nucleic acid in a sample comprising:
   a) hybridizing to the *M. kansasii* nucleic acid, if present, an oligonucleotide probe selected from the group consisting of SEQ ID NO:1, nucleotides 213–493 of SEQ ID NO:1, nucleotides 221–370 of SEQ ID NO:1 and nucleotides 351–490 of SEQ ID NO:1, and;
   b) detecting hybridization of the probe as an indication of the presence of *M. kansasii* nucleic acid in the sample.

8. The method of claim 7 wherein the probe is tagged with a detectable label.

9. The method of claim 8 wherein the detectable label is selected from the group consisting of radioisotopes, fluorescent moieties, chemiluminescent agents, ligands and enzymes.

10. A method for detecting an *M. kansasii* target sequence in a sample comprising:
    a) hybridizing a first primer selected from the group consisting of SEQ ID NO:2, SEQ ID NO:6, SEQ ID NO:7, SEQ ID NO:9, SEQ ID NO:11 and SEQ ID NO:12 to a first strand of the target sequence, if present;
    b) hybridizing a second primer selected from the group consisting of SEQ ID NO:3 and SEQ ID NO:10 to a second strand of the target sequence complementary to the first strand of the target sequence, if present;
    c) extending the hybridized first and second primers to produce a first and a second primer extension product, respectively, and displacing the first and second primer extension products from the first and second strands of the target sequence;
    d) repeating steps (a), (b) and (c) such that the target sequence is amplified, and;
    e) detecting the amplified target sequence.

11. The method of claim 10 wherein the amplified target sequence is detected by hybridization to an oligonucleotide probe tagged with a detectable label.

12. The method of claim 11 wherein the detectable label is selected from the group consisting of radioisotopes, fluorescent moieties, chemiluminescent agents, ligands and enzymes.

13. The method of claim 10 wherein the amplified target sequence is detected by hybridization and extension of a primer tagged with a detectable label.

14. A method for detecting an *M. kansasii* target sequence in a sample comprising:
    a) hybridizing to a first strand of the target sequence, if present, a first amplification primer consisting of a first target binding sequence, a restriction endonuclease recognition site 5' to the first target binding sequence and a sufficient number of nucleotides 5' to the restriction endonuclease recognition site to allow binding of a restriction endonuclease, the first target binding sequence being selected from the group consisting of SEQ ID NO:9, SEQ ID NO: 11 and SEQ ID NO: 12;
    b) hybridizing to a second strand of the target sequence complementary to the first strand of the target sequence, if present, a second amplification primer consisting of a second target binding sequence, the restriction endonuclease recognition site 5' to the first target binding sequence and a sufficient number of nucleotides 5' to the restriction endonuclease recognition site to allow binding of a restriction endonuclease, the second target binding sequence consisting of SEQ ID NO:10;
    c) amplifying the target sequence using an amplification method comprising the steps of extending the hybridized first and second amplification primers on the first and second strands of the target sequence, nicking the restriction endonuclease recognition site and displacing the extended first and second amplification primers, and;
    d) detecting the amplified target sequence.

15. The method of claim 14 wherein the extended first and second amplification primers are displaced by hybridization and extension of a first and a second bumper primer.

16. The method of claim 15 wherein the first bumper primer is selected from the group consisting of SEQ ID NO:5 and SEQ ID NO:8 and the second bumper primer consists of SEQ ID NO:4.

17. The method of claim 14 wherein the restriction endonuclease recognition site is a recognition site for HincII.

18. A method for detecting an *M. kansasii* target sequence in a sample comprising:
    a) hybridizing to a first strand of the target sequence, if present, a first amplification primer selected from the group consisting of SEQ ID NO:2, SEQ ID NO:6 and SEQ ID NO:7;
    b) hybridizing to a second strand of the target sequence complementary to the first strand of the target sequence, if present, a second amplification primer consisting of SEQ ID NO:3;
    c) amplifying the target sequence by Strand Displacement Amplification (SDA), and;
    d) detecting the amplified target sequence.

* * * * *

UNITED STATES PATENT AND TRADEMARK OFFICE
CERTIFICATE OF CORRECTION

PATENT NO. : 5,518,884
DATED : May 21, 1996
INVENTOR(S) : Patricia A. Spears et al It is certified that error appears in the above-indentified patent and that said Letters Patent is hereby corrected as shown below:

On the title page,

In the Title: Change "MYCIBACTERIUM" to --MYCOBACTERIUM--

NUCLEIC ACID SEQUENCES SPECIFIC FOR MYCOBACTERIUM KANSASII

Signed and Sealed this

Sixth Day of August, 1996

*Attest:*

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 493 base pairs
        ( B ) TYPE: nucleic acid
        ( C ) STRANDEDNESS: double
        ( D ) TOPOLOGY: linear     ( i i ) MOLECULE TYPE: DNA (genomic)

( v i ) ORIGINAL SOURCE:
        ( A ) ORGANISM: Mycobacterium kansasii     ( x i ) SEQUENCE DESCRIPTION: SEQ ID NO:1:

```
GATCGTCACC  CCAGCAGTTG  GTGGTCGGCA  GCATACTGGC  CGCCTGCGTG  CGATNNGCCG      60

CCCCGGTCTT  GATCACCGAG  AGTCTCAACT  TGCCCCCGGA  GCCTTGAGCT  GACCTGGCGC     120

TCGTTGGGAG  AGATCGTTGC  CGGCGTCGGA  TTCCTGGCGG  TGTTTGTCTA  CTGGCAGTCG     180

GTCAACACCC  GCGAACCACT  GATTCCCCTG  AAGATCCGCC  GCCGCACAAC  TGCTGGCCGG     240

GCATGACACC  GACCCATCAG  TCAGCGAATC  CTCCGCTGCA  TCAAATGAAT  CCACAGTCAT     300

CGACCTGTCC  GTCTATAGCG  GGCAGCCCAG  AAAAGGACCT  TAAATGACCG  CTACCCACGC     360

ACGCCGAAGA  CCAGCCGGGC  CGCGAGTACC  GAGTCGCCGG  CTCAGTCGGC  CAGTCGCTAT     420

CAGCACGTGC  GCTCGCATCT  GGCCGAACTC  AAACTGCACG  CCGCCGCTGA  AGCCCTGCCC     480

GCCGTCCTGG  ATC                                                          493
```

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Mycobacterium kansasii ( i x ) FEATURE:
    ( A ) NAME/KEY: primer_bind
    ( B ) LOCATION: 25..37
    ( D ) OTHER INFORMATION: /standard_name="target binding
        sequence"

( i x ) FEATURE:
    ( A ) NAME/KEY: misc_feature
    ( B ) LOCATION: 19..24
    ( D ) OTHER INFORMATION: /product="restriction endonuclease
        recognition site"

( x i ) SEQUENCE DESCRIPTION: SEQ ID NO:2:

TTGAATAGTC GGTTACTTGT TGACTCAGCG AATCCTC                37

( 2 ) INFORMATION FOR SEQ ID NO:3:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium kansasii ( i x ) FEATURE:
        ( A ) NAME/KEY: primer_bind
        ( B ) LOCATION: 25..37
        ( D ) OTHER INFORMATION: /standard_name="target binding
            sequence"

( i x ) FEATURE:
        ( A ) NAME/KEY: misc_feature
        ( B ) LOCATION: 19..24
        ( D ) OTHER INFORMATION: /product="restriction endonuclease
            recognition site"

( x i ) SEQUENCE DESCRIPTION: SEQ ID NO:3:

TTGAAGTAAC CGACTATTGT TGACTAGACG GACAGGT                37

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium kansasii ( x i ) SEQUENCE DESCRIPTION: SEQ ID NO:4:

CACAACTGCT GGC                13

( 2 ) INFORMATION FOR SEQ ID NO:5:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium kansasii ( x i ) SEQUENCE DESCRIPTION: SEQ ID NO:5:

TGATAGCGAC TGG                                                                                                13

(2) INFORMATION FOR SEQ ID NO:6:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Mycobacterium kansasii (ix) FEATURE:
        (A) NAME/KEY: primer_bind
        (B) LOCATION: 25..37
        (D) OTHER INFORMATION: /standard_name="target binding
              sequence"

(ix) FEATURE:
        (A) NAME/KEY: misc_feature
        (B) LOCATION: 19..24
        (D) OTHER INFORMATION: /product="restriction endonuclease
              recognition site"

(xi) SEQUENCE DESCRIPTION: SEQ ID NO:6:

TTGAATAGTC GGTTACTTGT TGACCGAATC CTCCGCT                                                                      37

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Mycobacterium kansasii (ix) FEATURE:
        (A) NAME/KEY: primer_bind
        (B) LOCATION: 25..37
        (D) OTHER INFORMATION: /standard_name="target binding
              sequence"

(ix) FEATURE:
        (A) NAME/KEY: misc_feature
        (B) LOCATION: 19..24
        (D) OTHER INFORMATION: /product="restriction endonuclease
              recognition site"

(xi) SEQUENCE DESCRIPTION: SEQ ID NO:7:

TTGAATAGTC GGTTACTTGT TGACAATCCT CCGCTGC                                                                      37

(2) INFORMATION FOR SEQ ID NO:8:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Mycobacterium kansasii (xi) SEQUENCE DESCRIPTION: SEQ ID NO:8:

GGGTAGCGGT CAT                                                                                                13

( 2 ) INFORMATION FOR SEQ ID NO:9:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( i i ) MOLECULE TYPE: DNA (genomic)

( v i ) ORIGINAL SOURCE:
      ( A ) ORGANISM: Mycobacterium kansasii ( x i ) SEQUENCE DESCRIPTION: SEQ ID NO:9:

TCAGCGAATC CTC                                                      13

( 2 ) INFORMATION FOR SEQ ID NO:10:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( i i ) MOLECULE TYPE: DNA (genomic)

( v i ) ORIGINAL SOURCE:
      ( A ) ORGANISM: Mycobacterium kansasii ( x i ) SEQUENCE DESCRIPTION: SEQ ID NO:10:

TAGACGGACA GGT                                                      13

( 2 ) INFORMATION FOR SEQ ID NO:11:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( i i ) MOLECULE TYPE: DNA (genomic)

( v i ) ORIGINAL SOURCE:
      ( A ) ORGANISM: Mycobacterium kansasii ( x i ) SEQUENCE DESCRIPTION: SEQ ID NO:11:

CGAATCCTCC GCT                                                      13

( 2 ) INFORMATION FOR SEQ ID NO:12:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( i i ) MOLECULE TYPE: DNA (genomic)

( v i ) ORIGINAL SOURCE:
      ( A ) ORGANISM: Mycobacterium kansasii ( x i ) SEQUENCE DESCRIPTION: SEQ ID NO:12:

AATCCTCCGC TGC                                                      13